United States Patent [19]

Hoppe et al.

[11] Patent Number: 5,347,853
[45] Date of Patent: Sep. 20, 1994

[54] METHOD OF AND APPARATUS FOR ASCERTAINING THE HARDNESS OF ROD-SHAPED ARTICLES OF THE TOBACCO PROCESSING INDUSTRY

[75] Inventors: Reinhard Hoppe, Marschacht; Rolf Lindemann, Glinde; Henning Möller, Hamburg, all of Fed. Rep. of Germany

[73] Assignee: Hörber AG, Hamburg, Fed. Rep. of Germany

[21] Appl. No.: 127,887

[22] Filed: Sep. 27, 1993

Related U.S. Application Data

[63] Continuation of Ser. No. 894,060, Jun. 5, 1992, abandoned.

[30] Foreign Application Priority Data

Jun. 15, 1991 [DE] Fed. Rep. of Germany ....... 4119821

[51] Int. Cl.$^5$ .............................................. G01N 3/48
[52] U.S. Cl. ............................................ 73/82; 131/906
[58] Field of Search ................ 73/78, 79, 81, 82; 131/906–910, 84.1–84.4; 356/381, 385, 386

[56] References Cited

U.S. PATENT DOCUMENTS

| | | | |
|---|---|---|---|
| 3,192,389 | 6/1965 | Schmesmund | 73/81 |
| 3,850,029 | 11/1974 | Swanson | 73/81 |
| 4,011,950 | 3/1977 | McLoughlin et al. | 250/208.2 |
| 4,201,475 | 5/1980 | Bodlaj | 356/381 |
| 4,311,392 | 1/1982 | Yazaki et al. | 356/381 |
| 4,326,542 | 4/1982 | Laszlo et al. | 131/906 |
| 4,567,752 | 2/1986 | Labbe | 73/37.6 |
| 4,974,443 | 12/1990 | Heitmann | 73/81 |
| 5,075,559 | 12/1991 | Amir | 356/381 |

FOREIGN PATENT DOCUMENTS 1932973 10/1977 Fed. Rep. of Germany ......... 73/81

*Primary Examiner*—Robert Raevis
*Attorney, Agent, or Firm*—Darby & Darby

[57] ABSTRACT

The reliability of mechanical testing of the hardness of cigarettes with one or more pivotable weights is enhanced by modifying the results of such testing on the basis of signals which are obtained by optically scanning the diameters of successive cigarettes prior to mechanically induced deformation. Optical scanning is carried out by triangulation with a fixedly mounted measuring head. The signals which are obtained with mechanical testing can be further influenced by taking into consideration the moisture content and/or the temperature of tobacco in tested cigarettes.

16 Claims, 2 Drawing Sheets

METHOD OF AND APPARATUS FOR ASCERTAINING THE HARDNESS OF ROD-SHAPED ARTICLES OF THE TOBACCO PROCESSING INDUSTRY

This is a continuation of application Ser. No. 07/894,060, filed Jun. 5, 1992, now abandoned.

CROSS-REFERENCE TO RELATED CASE

The method and apparatus of the present invention constitute an improvement over and a further development of the method and apparatus disclosed in commonly owned copending patent application Ser. No. 07/857,733 filed Mar. 26, 1992 by Reinhard Hoppe and Rolf Lindemann for "Method of and apparatus for ascertaining the diameters of rod-shaped articles".

BACKGROUND OF THE INVENTION

The invention relates to improvements in methods of and in apparatus for ascertaining the hardness of elastically deformable rod-shaped articles of the tobacco processing industry. More particularly, the invention relates to improvements in methods of and in apparatus for mechanically testing plain or filter cigarettes, cigars, cigarillos, cheroots and/or other rod-shaped articles of the tobacco processing industry for the purpose of ascertaining their hardness.

Commonly owned U.S. Pat. No. 4,974,443, granted Dec. 4, 1990 to Uwe Heitmann for "Method of and apparatus for ascertaining the hardness of cigarettes and the like" discloses the utilization of one or more pivotable levers which act not unlike weights and subject successive cigarettes of a series of such rod-shaped articles to a radially oriented deforming action. The extent of mechanically induced deformation is measured, and the results of such measurement are utilized to regulate the operation of the cigarette rod making or filter tipping machine in order to ensure that the hardness of cigarettes will match an optimum value. The articles to be tested are moved sideways, i.e., substantially at right angles to their longitudinal axes, and each lever can simultaneously deform two or more cigarettes of such series.

As used herein, the term "hardness" is intended to denote the resistance of rod-shaped articles of the tobacco processing industry (hereinafter referred to as cigarettes or filter cigarettes but intended to embrace all kinds of rod-shaped articles of the tobacco processing industry which contain filter material for tobacco smoke and/or natural, reconstituted and/or substitute tobacco) to elastic deformation of their fillers in response to the application of mechanical stresses to the external surfaces of their wrappers. For example, such mechanical stress will be applied by the fingers of a person who is about to light or who is in the process of smoking a cigarette. The hardness of cigarettes is a function of the so-called filling power of shreds or filaments of tobacco or filter material. The filling power is the ability of a predetermined quantity of tobacco or filter material to fill the tubular wrapper of a rod-shaped article of the tobacco processing industry. Thus, the filling power is clearly related to the hardness of cigarettes.

A plain or filter cigarette is likely to be subjected to a number of mechanical and/or other deforming stresses before it reaches the hardness testing station. For example, a filter cigarette is likely to be mechanically deformed (so that its cross-sectional outline is not an ideal circular outline) during subdivision of a continuous cigarette rod into plain cigarettes of unit length or multiple unit length, during the application of uniting bands of tipping paper which are used to connect plain cigarettes with filter plugs (such application involves rolling the uniting bands around coaxial plain cigarettes and filter plugs), during severing of filter plugs to divide filter cigarettes of double unit length into filter cigarettes of unit length, as well as during repeated transfer of cigarettes and their components from conveyor to conveyor which often involves attracting the cigarettes by suction and/or pressing the cigarettes against the peripheries of rotary conveyors by shrouds and/or other mechanical means. Each such treatment is likely to affect the cross-sectional outline of the cigarettes ahead of the mechanical hardness testing station. A frequent deformation is that which imparts to the cigarettes an oval shape and is likely to greatly affect the accuracy of mechanical hardness measurements which are based on the presumption that a cigarette to be tested has an ideal circular cross-sectional outline. An oval cigarette is held on its conveyor or conveyors in a predetermined orientation which does not change ahead of or at the hardness testing station because, as a rule, the cigarettes are attracted to their conveyors by suction. In other words, an oval cigarette is not likely to change its cross-sectional outline on the way toward the mechanical hardness testing station because it is not permitted to roll, i.e., to perform a movement which would be likely to at least partially restore its desirable circular cross-sectional outline. As a rule, testing of hardness is carried out while the cigarettes are confined in axially parallel peripheral flutes of a rotary drum-shaped conveyor having suction ports which communicate with the flutes and attract the cigarettes to the rotary conveyor, An oval cigarette which has entered a flute of such conveyor will remain oval during advancement past the mechanical hardness testing instrumentality or instrumentalities.

OBJECTS OF THE INVENTION

An object of the invention is to provide a novel and improved method which ensures more reliable measurements of the hardness of cigarettes or like rod-shaped articles of the tobacco processing industry.

Another object of the invention is to provide a method of correcting mechanical measurements of the hardness of cigarettes for the purpose of compensating for eventual deviation of the shapes of cigarettes to be mechanically tested from an optimum shape.

A further object of the invention is to provide a method which renders it possible to accurately determine the hardness of oval or otherwise deformed cigarettes.

An additional object of the invention is to provide a novel and improved method of scanning cigarettes or analogous rod-shaped articles of the tobacco processing industry ahead of the mechanical hardness testing station.

Still another object of the invention is to provide a method which renders it possible to correct the results of mechanical hardness testing in one or more respects.

A further object of the invention is to provide a novel and improved apparatus for the practice of the above outlined method.

An additional object of the invention is to provide an apparatus which constitutes an improvement over and a further development of the apparatus disclosed in commonly owned U.S. Pat. No. 4,974,443 to Heitmann.

Another object of the invention is to provide the apparatus with novel and improved means for correcting signals which are obtained as a result of mechanical determination of the hardness of cigarettes or other rod-shaped articles of the tobacco processing industry.

Still another object of the invention is to provide an apparatus which can correct signals denoting the results of mechanical testing of cigarettes or the like on the basis of parameters other than the shape of articles prior to mechanical testing.

A further object of the invention is to provide a rod making machine which embodies an apparatus of the above outlined character.

An additional object of the invention is to provide a filter tipping machine which embodies an apparatus of the above outlined character.

Another object of the invention is to provide a production line for the making of filter cigarettes or analogous rod-shaped articles of the tobacco processing industry which embodies one or more apparatus of the above outlined character.

SUMMARY OF THE INVENTION

One feature of the present invention resides in the provision of a method of ascertaining the hardness of elastically deformable rod-shaped articles of the tobacco processing industry. The improved method comprises the steps of advancing a series of articles in a predetermined direction along a predetermined path wherein the longitudinal axes of the articles are at least substantially normal to the predetermined direction, subjecting the articles of the series to elastic deformation in a first portion of the path including applying to the articles a predetermined deforming force substantially radially of the articles whereby the articles develop depressions and the extent of elastic deformation is indicative of the hardness of deformed articles, monitoring the extent of elastic deformation and generating first signals which denote the monitored deformation, optically scanning at least one characteristic of the articles of the series in a second portion of the path upstream of the first portion and generating second signals which denote the at least one characteristics, and modifying the first signals in dependency upon the respective second signals.

The scanning step can include determining a variable reference point as a function of the thickness of the respective article, and the monitoring step of such method can include utilizing the reference point as a starting point for measurement of the extent of deformation of the respective article in the first portion of the path.

The scanning step can include measuring the distance of the external surfaces of articles from a predetermined fixed reference point, and the second signals then indicate the measured distance and hence the diameters of the respective (undeformed) articles. The advancing step of such method can comprise conveying the articles along the first portion of the path on a mobile support, and such method can further comprise the step of measuring the distance of the support from the fixed reference point. This is indicative of the diameter (thickness) of an article in the second portion of the path plus the distance of the external surface of such article from the fixed reference point. Thus, the diameter (thickness) of an article prior to deformation in the first portion of the path can be calculated by the simple expedient of deducting the distance between the variable reference point and the fixed reference point from the distance between the fixed reference point and the support.

The monitoring step can include determining the thickness of deformed articles in the first portion of the path, and the scanning step can comprise determining the thickness of yet to be deformed articles in the second portion of the path. The modifying step of such method can comprise determining the difference between the thicknesses of an article in the first and second portions of the path because such difference corresponds to the extent of deformation of the article and is thus indicative of the hardness of the respective article.

If the articles contain tobacco, the moisture content of such tobacco (and more particularly fluctuations of the moisture content) can influence the hardness of the articles. Therefore, the method can further comprise the steps of monitoring the moisture content of tobacco in the articles, generating third signals which denote the monitored moisture content, and modifying the second and/or first signals in dependency on the third signals.

Changes in temperature of tobacco in the articles can also influence the hardness of the articles. Therefore, the improved method can further comprise the steps of monitoring the temperature of tobacco in the articles, generating additional signals which denote the monitored temperature, and modifying the second and/or first signals in dependency on the additional signals.

Another feature of the present invention resides in the provision of an apparatus for ascertaining the hardness of elastically deformable rod-shaped articles of the tobacco processing industry. The improved apparatus comprises means for advancing a series of articles in a predetermined direction along a predetermined path wherein the longitudinal axes of the articles are at least substantially normal to the predetermined direction, a combined mechanical monitoring and deforming unit having means for subjecting the articles of the series to elastic deformation in a first portion of the path including means for applying to the articles a predetermined deforming force radially of the articles whereby the articles develop depressions and the extent of elastic deformation is indicative of the hardness of deformed articles, means for monitoring the extent of elastic deformation of articles including means for generating first signals denoting the monitored deformation, means for optically scanning at least one characteristic (such as diameter, i.e., thickness) of the articles of the series in a second portion of the path upstream of the first portion including means for generating second signals which denote the at least one characteristic, and signal processing means including means for modifying the first signals in dependency on the respective second signals.

The advancing means preferably comprises at least one rotary conveyor having peripheral article-receiving flutes. The scanning means can include means for measuring the thickness of the articles radially of the at least one rotary conveyor, and the second signals are preferably indicative of variable reference values, such as the distance of the external surface of the scanned article from a fixed reference point on the scanning means, and the means for generating first signals can include means for utilizing the reference values as starting points for monitoring the extent of elastic deformation of articles in the first portion of the path. Thus, if the starting point is the distance of the radially outermost portion of a yet to be elastically deformed article from the fixed reference point on the scanning means, the difference between such distance and the distance of the bottom of the flute from the fixed reference point is indicative of the thickness or diameter of the article prior to deformation.

The scanning means can comprise a measuring head which defines the fixed reference point adjacent the first portion of the path. The means for generating second signals can comprise means for generating signals which denote the distance of the surfaces of articles in the second portion of the path from the fixed reference point and means for converting signals which denote such distances into signals which denote the thickness of the respective articles. The rotary conveyor is disposed at a predetermined distance from the fixed reference point on the measuring head. The signal converting means of the modifying means in such apparatus preferably includes a memory for a third signal which denotes the predetermined distance and means for generating further signals which denote the differences between the third signal and the signals denoting the distances of the surfaces of articles in the second portion of the path from the fixed reference point. The measuring means can include means for directing at least one beam of radiation upon articles in the second portion of the path whereby the articles reflect at least a portion of the at least one beam. The measuring means (such as the aforementioned measuring head) can include means for intercepting the reflected portion of the at least one beam. The measuring means is preferably designed to triangulate the at least one characteristic of articles in the second portion of the path.

The signal processing means of the improved apparatus can comprise means for evaluating the first signals and means for evaluating the second signals. The modifying means of such signal processing means can comprise a computer which has inputs for the evaluated first and second signals and serves to generate signals denoting the differences between the evaluated first signals and the respective evaluated second signals.

If the articles contain moist tobacco, fluctuations of the moisture content are likely to distort the results of determination of the hardness. Therefore, the apparatus can further comprise means for generating third signals which denote the moisture content of tobacco, and the signal processing means of such apparatus then comprises means for modifying the second and/or first signals as a function of third signals.

The temperature of tobacco in the rod-shaped articles is also a parameter which is likely to affect the accuracy of determination of the hardness of such articles. Therefore, the improved apparatus can be further provided with means for generating signals denoting the moisture content of tobacco in the articles, and the signal processing means of such apparatus further comprises means for modifying the second signals and/or the first signals as a function of signals which denote the temperature of tobacco.

The novel features which are considered as characteristic of the invention are set forth in particular in the appended claims. The improved apparatus itself, however, both as to its construction and its mode of operation, together with additional features and advantages thereof, will be best understood upon perusal of the following detailed description of certain presently preferred specific embodiments with reference to the accompanying drawing.

DESCRIPTION OF PREFERRED EMBODIMENTS

Figure 1:
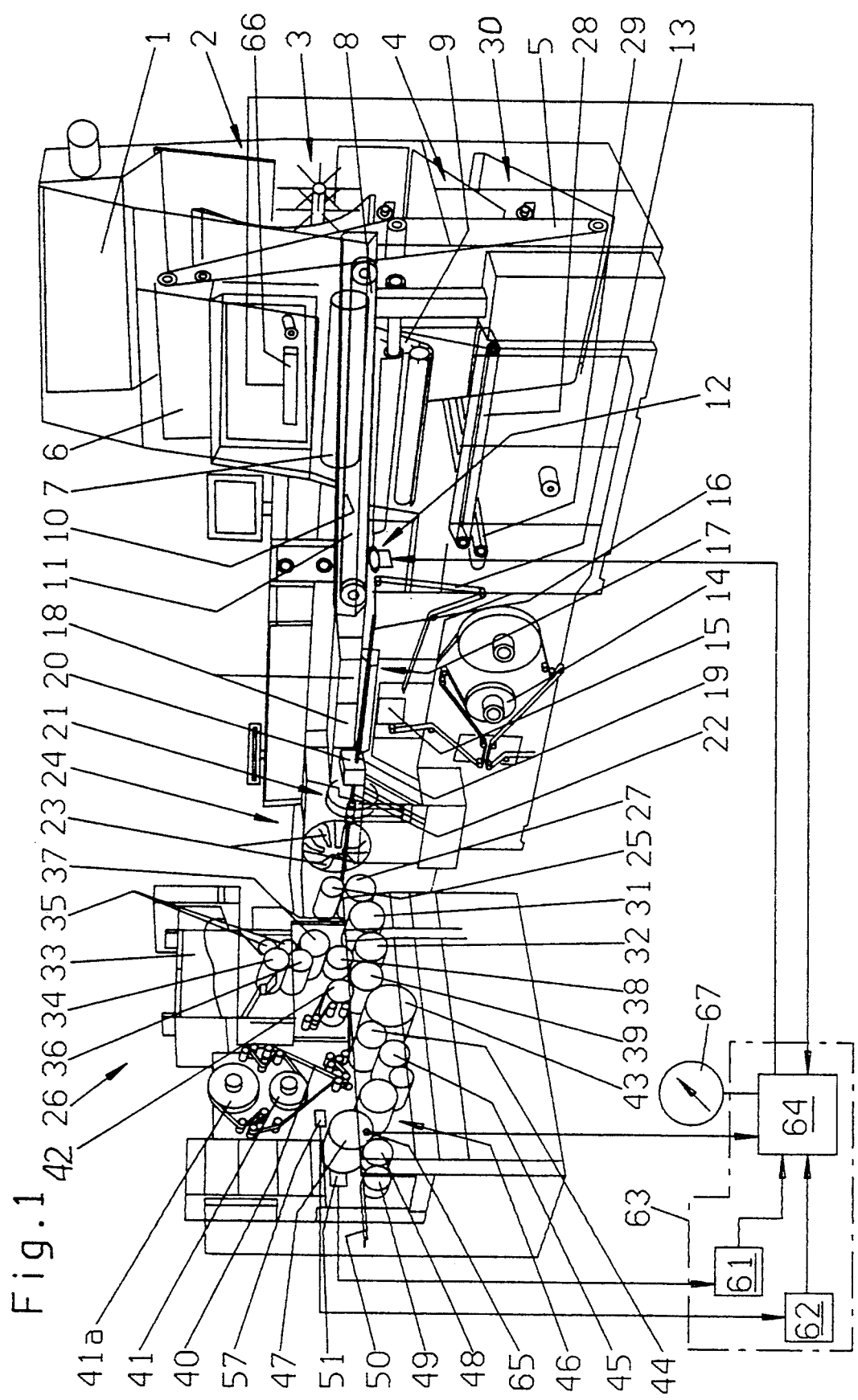
FIG. 1 is a schematic perspective view of a production line including a cigarette rod making machine and a filter tipping machine, an apparatus which embodies the invention being installed in the filter tipping machine.

The construction and mode of operation of the combination of a cigarette rod making machine and a filter tipping machine shown in FIG. 1 are as follows:

The cigarette rod making machine comprises a gate 1 which serves to discharge batches of tobacco particles into a first distributor 2. The latter is adjacent a rotary evacuating member 3 having vanes or paddles which transfer tobacco particles at a controlled rate into the main magazine 4 of a second or main distributor (also called hopper). One sidewall of the magazine 4 is constituted by the upwardly moving reach of an endless elevator conveyor 5 which delivers accurately metered portions or batches of tobacco particles into an upright gathering duct 6. The open lower end of the duct 6 is adjacent a carded drum 7 which draws a continuous layer of tobacco particles past a rapidly rotating picker roller 8. The pins of the picker roller 8 expel tobacco particles from the carding of the conveyor 7 and propel the thus liberated particles against a suitably configurated guide 9 simultaneously with pneumatic segregation of heavier tobacco particles (such as fragments of tobacco ribs). Satisfactory tobacco particles form a thin layer which is propelled against the underside of the lower reach of a foraminous stream building conveyor 10. This conveyor cooperates with a suction chamber 11 to build a continuous tobacco stream which contains a surplus of tobacco particles. The surplus is removed by a conventional adjustable trimming or equalizing device 12 serving to convert the stream into a rod-like filler which is caused to advance onto the upper side of a running web 13 of cigarette paper or other suitable wrapping material. The web 13 is drawn off a bobbin 14 which stores an expiring supply of cigarette paper, and such web is caused to pass through an imprinting mechanism 15 before it reaches an endless belt conveyor 16 (known as garniture) which draws the web and the tobacco filler through a wrapping mechanism 17 having means for draping the web around the filler to thus form a partly finished cigarette rod wherein one longitudinally extending marginal portion of the convoluted web 13 projects from the other marginal portion substantially tangentially of the rod. The projecting marginal portion of the draped web 13 is coated with a suitable adhesive which is discharged by a paster (not shown), and the adhesive-coated marginal portion is folded over the other marginal portion to form therewith a longitudinally extending seam. Such seam is heated by a tandem sealer 18 in order to promote setting of the adhesive and to strengthen the seam before the thus finished cigarette rod 19 is caused to pass through a density measuring apparatus 20 of any known design. The leader of the finished rod 19 is severed at selected intervals by a so-called cutoff 21 so that the rod 19 yields a succession of discrete plain cigarettes 22, e.g., plain cigarettes of double unit length.

Conveyor belts 28, 29 are provided to transport trimmed off surplus tobacco from the trimming device 12 into a collecting receptacle 30 beneath the magazine 4 of the main distributor or hopper so that the returned surplus can be entrained by the elevator conveyor 5 for renewed delivery into the gathering duct 6.

Successive plain cigarettes 22 of double unit length are grasped by the controlledly movable arms 23 of a rotary transfer mechanism 24 which deposits the plain cigarettes in successive axially parallel peripheral flutes of a rotary drum-shaped conveyor 25 forming part of the filter tipping machine 26. The conveyor 25 delivers the cigarettes 22 into the flutes of a rotary drum shaped severing conveyor 27 cooperating with a rotary circular knife (not shown) which divides each cigarette 22 into two plain cigarettes of unit length.

The severing conveyor 27 of the filter tipping machine 26 delivers pairs of plain cigarettes of unit length to two aligning and spreading conveyors 31 which deposit pairs of axially spaced apart coaxial plain cigarettes into successive axially parallel peripheral flutes of a rotary drum-shaped assembly conveyor 32. The filter tipping machine 26 further comprises a magazine 33 for a supply of filter rod sections of six times unit length. The magazine 33 discharges such filter rod sections into the flutes of a rotary drum-shaped severing conveyor 34 which cooperates with two rotary circular knives 35 serving to subdivide each filter rod section of six times unit length into a row of three coaxial filter rod sections or plugs of double unit length. The filter plugs of successive rows are staggered on a staggering conveyor 36 and are thereupon shuffled on a shuffling conveyor 37 which converts them into a single file of parallel filter plugs, and successive plugs of such single file enter successive flutes of a combined rotary cylindrical drum-shaped accelerating and inserting conveyor 38. The latter inserts discrete filter plugs of double unit length into the spaces between pairs of plain cigarettes of unit length on the assembly conveyor 32 so that the flutes of the conveyor 32 accumulate groups of three coaxial rod-shaped articles each (group) including a filter plug of double unit length flanked by two plain cigarettes of unit length. The assembly conveyor 32 delivers such groups into successive flutes of a rotary drum-shaped condensing conveyor 39 whereon the plain cigarettes are caused to abut the adjacent ends of the respective filter plugs.

A bobbin or reel 41 on the frame of the filter tipping machine 26 stores a supply of expiring web 40 of tipping paper one side of which is coated with adhesive ahead of a cutting drum 42 cooperating with a rotary knife. A supply of fresh tipping paper (note the bobbin or reel 41a) is maintained in a state of readiness, and its leader is spliced to the expiring web 40 (supplied by the reel 41) as soon as the supply of web 40 is nearly exhausted.

The cutting drum 42 supplies a series of adhesive-coated uniting bands (sections of web 40) which are attached to successive groups in the flutes of the conveyor 39 before the latter delivers the groups, and the respective uniting bands, onto a rolling drum 43. The drum 43 convolutes the uniting bands around the respective filter plugs and the adjacent inner end portions of the respective plain cigarettes to form filter cigarettes of double unit length, and the drum 43 delivers finished filter cigarettes into the flutes of an intermediate conveyor 44 which is used to expel moisture from the convoluted uniting bands. The thus dried filter cigarettes are transferred onto a severing drum 45 cooperating with a rotary circular knife (not shown) to divide each filter cigarette of double unit length into two filter cigarettes of unit length. Each filter cigarette of double unit length is severed midway across the respective filter plug and the convoluted uniting band.

Figure 2:
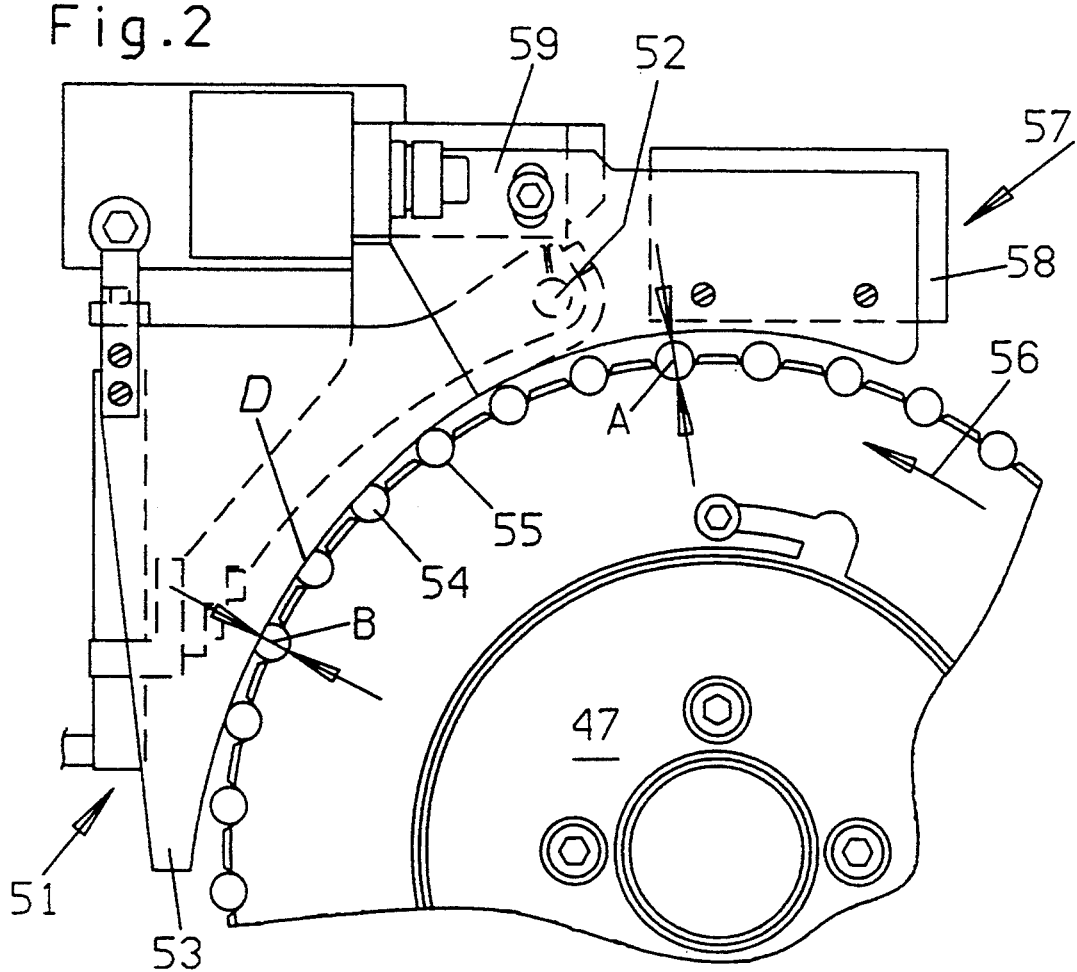
FIG. 2 is an enlarged fragmentary front elevational view of a portion of the filter tipping machine of FIG. 1 and shows certain constituents of the mechanical monitoring and optical scanning devices of the improved apparatus.

The thus obtained two rows of filter cigarettes of unit length are caused to advance with the rotary drum-shaped conveyors of a turn-around device 46 which inverts the filter cigarettes of one row and places them into the gaps between successive (non-inverted) filter cigarettes of the other row to form a single row of filter cigarettes wherein the filters of all cigarettes face in the same direction. The last conveyor of the turn-around device 46 delivers successive filter cigarettes of the single row into the axially parallel peripheral flutes 55 (FIG. 2) of a testing conveyor 47 and thence into the flutes of an ejecting conveyor 48 serving to segregate defective filter cigarettes from satisfactory articles. The ejecting conveyor 48 further comprises or cooperates with means for monitoring the tobacco-containing ends or heads of successive filter cigarettes of unit length. A rotary drum-shaped conveyor 49 accepts satisfactory filter cigarettes from the ejecting conveyor 48 and deposits them on the upper reach of an endless take-off conveyor 50.

The heretofore described parts of the production line including the cigarette making and filter tipping machines shown in FIG. 1 are known and form no part of the present invention. The cigarette rod making machine can be of the type known as PROTOS which is distributed by the assignee of the present application, and the filter tipping machine 26 can be of the type known as MAX (also distributed by the assignee of the present application).

The testing conveyor 47 cooperates with a monitoring device 51 which serves to ascertain the hardness of filter cigarettes 54 (FIGS. 2 and 3) of unit length. The monitoring device 51 comprises at least one lever 53 which is pivotable about the axis of a shaft 52 and bears, at least with its own weight, against a series of successive filter cigarettes 54 while the cigarettes advance along an arcuate path in the direction of arrow 56 shown in FIG. 2. The cigarettes 54 which are being acted upon by the illustrated lever 53 in the radial direction of the conveyor 47 are received in the axially parallel peripheral flutes 55 each having the same depth and each receiving, for example, approximately one-half of the respective filter cigarette. The cigarettes 54 are elastically deformable, and the extent of their deformation (i.e., the depth of depressions provided therein by the lever 53) is indicative of their hardness.

The monitoring device 51 is adjacent a first portion of the arcuate path for the filter cigarettes 54 in the flutes 55 of the conveyor 47, namely downstream of a second portion which is adjacent an optical scanning device 57. The latter includes a so-called measuring head or range finder 58 which is designed to emit a beam 100 of radiation (e.g., visible light) against the external surfaces 54a of tubular wrappers of successive (yet to be deformed) filter cigarettes 54 advancing along the second portion of their path toward the first portion, i.e., toward the monitoring device 51. The purpose of the optical scanning device 57 is to ascertain certain dimensions (particularly the thickness or diameter A) of each cigarette 54 which is on its way toward the monitoring device 51.

The diameters A of all cigarettes 54 which reach the scanning device 57 are not the same. This is due to certain deformation of cigarettes 54 during making of plain cigarettes in the cigarette rod making machine as well as during assembly of plain cigarettes and filter plugs into filter cigarettes of double unit length and unit length. In many instances, the cigarettes 54 which reach the measuring head 58 of the scanning device 57 are slightly oval, i.e., their cross-sectional outline departs from an ideal circular outline. If the cigarettes 54 are out of round before they reach the lever 53 of the monitoring device 51, and particularly if their deformation is pronounced in the radial direction of the conveyor 47 (i.e., in the direction of action of the lever 53 upon the adjacent cigarettes 54), deformation which is detected while the cigarettes 54 are acted upon by the lever 53 is likely to be misleading, i.e., it will not be truly indicative of the hardness of the respective cigarettes.

The measuring head 58 of the scanning device 57 is fixedly mounted adjacent the second portion of the path for filter cigarettes 54 in the respective flutes 55 of the conveyor 47 and establishes a fixed reference point FRP at a predetermined distance AR from the deepmost portion of that flute 55 which is nearest to the measuring head 58. The distance AM of the fixed reference point FRP from the nearest cigarette 54 can vary from cigarette to cigarette because it is indicative of the distance of the fixed reference point FRP from the radially outermost portion of the external surface 54a of the tubular wrapper of cigarette 54 at the scanning station 60 (best shown in FIG. 3). The measuring head 58 is mounted on a fixedly installed carrier 59 for the shaft 52 of the lever 53 forming part of the monitoring device 51.

The measuring head 58 is designed to emit the at least one beam 100 of radiation, and at least a portion (shown at 100a) of such beam is reflected back toward the measuring head by the external surface 54a of the tubular wrapper of the filter cigarette 54 advancing through the scanning station 60. The operation of the measuring head 58 is based on the triangulation principle, and the purpose of this measuring head is to ascertain the fixed distance AR from the deepmost portion of the nearest flute 55 to the fixed reference point FRP (prior to actual testing of cigarettes 54) as well as to ascertain the distance AM between a variable reference point RP and the fixed reference point FRP, i.e., the shortest distance from the external surface 54a of the tubular wrapper of a cigarette 54 at the scanning station 60 from the head 59. The difference between the distances AR and AM equals the diameter A of the filter cigarette 54 in that flute 55 which is nearest to the fixed reference point FRP.

A presently preferred measuring head or range finder 58 is that known as type LC-ML-AT 30/3/10K which is distributed by the Firm Laser Components at D-8038 Gröbenzellt Federal Republic Germany.

The filter cigarettes 54 which advance through the scanning station 60 are attracted to the surfaces bounding the respective flutes 55, e.g., by providing the conveyor 47 with suction ports which are customary in conveyors for the transport of rod-shaped articles of the tobacco processing industry. The path of flutes 55 and of the cigarettes 54 therein is a circular path, and the fixed distance AR is known; such distance can be calculated (and a corresponding signal stored in a suitable memory of the signal processing unit 63 (FIG. 1) of the improved apparatus) by triangulation (i.e., by resorting to the measuring head 58) prior to start of the actual scanning operation, i.e., prior to determination of the diameters A of yet to be deformed filter cigarettes 54.

The signal generating component or components of the monitoring device 51 transmit signals denoting the reduced diameters or thicknesses B (FIG. 2) of successive deformed cigarettes 54 to a first evaluating circuit 61 of the signal processing unit 63 shown in the lower left-hand portion of FIG. 1. The measuring head 58 of the scanning device 57 transmits signals denoting the diameters A of filter cigarettes 54 to a second evaluating circuit 62 of the signal processing unit 63. The first signals which are supplied by the signal generating means of the monitoring device 51 are indicative of the extent of deformation (indicated in FIG. 2, as at D) of successive filter cigarettes 54, namely of the depth of radial depressions which are made by the lever 53 of the monitoring device 51. The signal generating means of the measuring head 58 transmits signals which are indicative of the diameters A of the articles 54 ahead of the monitoring device 51, i.e., of differences AR minus AM for successive cigarettes 54. The diameters A are measured in the radial direction of the conveyor 47.

The evaluating circuit 62 can be designed to average the signals denoting the diameters A of a certain number of successively conveyed filter cigarettes 54 and to make the thus obtained averaged second signals available for modification of the corresponding first signals furnished by the signal generating means of the monitoring device 51. The averaged first signals at the output of the evaluating circuit 61 are indicative of the average hardness of a selected number of successively monitored filter cigarettes. Analogously, the signal generating means of the monitoring device 51 can be designed to average selected numbers of successive first signals (denoting the diameters B or the extent of radial deformation of cigarettes 54 at the monitoring station downstream of the scanning station 60).

The outputs of the evaluating circuits 61, 62 are connected to the corresponding inputs of a computer 64 which forms part of the signal processing unit 63 and is designed to modify the first signals (from 61) in dependency upon the corresponding second signals (from 62) in order to take into consideration the fact that the diameters A of the cigarettes 54 reaching the scanning station 60 do not always match an optimum or desired diameter such as would be necessary to ensure that the lever 53 of the monitoring device 51 will subject each and every article 54 at the monitoring station to identical deforming action.

The temperature of tobacco in the filter cigarettes 54 is likely to vary while the filter tipping machine 26 is in operation. Variations of tobacco temperature are likely to result in a distortion of measurements which are carried out by the monitoring device 51. Therefore, the apparatus of the present invention preferably further comprises a temperature monitoring device 65 which transmits signals denoting the temperature of tobacco, and such signals are transmitted to the computer 64 which modifies the first signals accordingly. As a rule, heating of tobacco to an elevated temperature is likely to influence the operation of the monitoring device 51 in such a way that the first signals transmitted to the evaluating circuit 61 are indicative of a lesser hardness (i.e., of a hardness which is less than actual hardness), and that the presence of relatively cool tobacco will induce the device 51 to generate signals which indicate that the hardness of cigarettes 54 exceeds the actual hardness. The computer 64 modifies the first signals in dependency on the intensity and/or other characteristics of signals which are transmitted by the temperature monitoring device 65 so that the hardness signals at the output of the computer 64 more accurately reflect the actual hardness of the monitored cigarettes 54. The device 65 can be of the type known as KT15 distributed by the Firm Heimann, Federal Republic Germany. This device is installed in or adjacent the conveyor 47.

Fluctuations of the moisture content of tobacco in the cigarettes 54 are also likely to adversely influence the accuracy of first signals from the monitoring device 51 to the evaluating circuit 61 and thence to the computer 64. A higher moisture content of tobacco will induce the device 51 to generate first signals which are indicative of lesser than actual hardness, and a lower moisture content of tobacco will induce the device 51 to generate signals which are indicative of greater than actual hardness. Therefore, the improved apparatus further comprises a device 66 which determines the moisture content of tobacco (e.g., adjacent the gathering duct 6 of the cigarette rod making machine) and transmits appropriate signals to the computer 64 which processes such signals to modify the first signals from the evaluating circuit 61 and to thus ensure that the signals at the output of the computer are more accurately indicative of the actual hardness of tested articles 54. The device 66 can be of a type well known in the tobacco processing field, e.g., a moisture measuring device of the type distributed by the assignee of the present application.

Signals which are transmitted by the output of the computer 64 are displayed at 67 and/or utilized to control the operation of the surplus removing trimming or equalizing device 12 and to thus automatically compensate for deviations of actual hardness from desirable optimum hardness of the rod-like filler which is converted into the tobacco containing portion of the cigarette rod 19.

Figure 3:
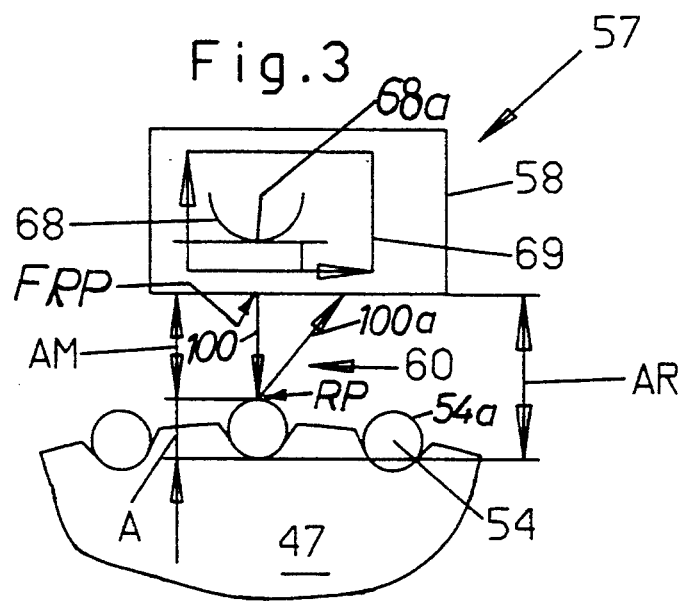
FIG. 3 is an enlarged view of a detail in FIG. 2.

The mode of operation of the improved hardness ascertaining apparatus is as follows:

The beam 100 at the scanning station 60 of FIG. 3 is used first while the flutes 55 of the conveyor 47 are empty, namely to ascertain the fixed distance AR from the fixed reference point FRP to the deepmost portion of the flute 55 at the scanning station 60, i.e., of the flute nearest to the measuring head 58. A corresponding signal is transmitted to and is stored as a reference signal in a memory of the signal processing unit 63.

The conveyor 47 thereupon begins to transport discrete filter cigarettes 54 in successive flutes 55, and the measuring head 58 proceeds to determine the distances AM, i.e., the distances of the fixed reference point FRP from the (non-fixed) reference points RP denoting the radially outermost portions of external surfaces 54a of tubular wrappers of cigarettes 54 at the scanning station 60. In order to enhance the accuracy of determination of the distance AM (which can vary from cigarette to cigarette), the measuring head 58 is preferably designed to store a series of signals denoting different distances of an article 54 advancing through the scanning station 60 from the fixed reference point FRP. This is indicated in FIG. 3 by a curve 68 within a window 69 of the measuring head 58. The measuring head 58 can select an extreme value (e.g., the value 68a denoting the shortest distance of an article 54 at the station 60 from the measuring head 58) for transmission of a corresponding (second) signal to the evaluating circuit 62 in the signal processing unit 63. The evaluating circuit 62 further receives the reference signal denoting the fixed distance AR and determines the distance AR−AM=A. A corresponding signal, denoting the diameter or thickness A of the article 54 at the station 60, is transmitted to the respective input of the computer 64 for use to modify the corresponding first signal from the evaluating circuit 61.

As mentioned above, the cigarettes 54 in the flutes 55 are preferably attracted to the conveyor 47 by suction (or are mechanically urged against the surfaces bounding the respective flutes 55) so that the orientation of cigarettes 54 relative to the conveyor 47 does not change during advancement from the scanning station 60 (measuring head 58) to the monitoring station (device 51). This ensures, that the lever 53 of the monitoring device 51 deforms the cigarettes 54 radially in the same direction in which the diameters A of the cigarettes were ascertained at the scanning station 60. Therefore, the ascertained distance AM or the variable reference point RP is preferably utilized as a starting distance or reference point for determination of the extent of radial deformation of successive cigarettes 54 by the lever 53. Otherwise stated, the monitoring device 51 can ascertain the distance between the radially outermost portions (point RP in FIG. 3) of the external surfaces 54a of the tubular wrappers of yet to be deformed cigarettes 54 and the flats D of the same cigarettes at the monitoring station. The corresponding (first) signals are transmitted to the evaluating circuit 61 which also receives the reference signal denoting the fixed distance AR so that it can transmit to the computer 64 signals denoting the radial thicknesses B of cigarettes 54 at the monitoring station adjacent the lever 53. The computer 64 thereupon ascertains for each filter cigarette 54 the difference A−B which is indicative of the extent of radial deformation of cigarettes by the lever 53 and of the hardness of the respective cigarettes. As mentioned above, the computer 64 can influence the difference A−B in dependency on signals from the temperature monitoring device 65 and/or from the moisture detector 66 to further reduce the likelihood of departure of indications at 67 from actual hardness of the respective filter cigarettes.

FIG. 1 shows a signal processing unit 63 in the form of a block diagram. Such illustration has been selected for convenience of description of the mode of operation of the signal processing unit 63. In actual practice, especially in sophisticated modern production lines for the making of plain or filter cigarettes, cigars, cigarillos or other rod-shaped articles of the tobacco processing industry, the signal processing unit 63 constitutes an integrated circuit of a computer which does not exhibit discrete components in the form of evaluating circuits, memories and/or others but performs all of the above functions with the same results.

The present invention is based on the recognition that the radial dimension (diameter A in FIG. 3) of a cigarette 54 prior to mechanical hardness testing at the station for the lever 53 is of considerable importance for the accuracy of mechanical determination of hardness because the lever 53 deforms successive cigarettes 54 in the same direction (radially of the conveyor 47) in which the measuring head 58 operates to measure the diameters A of cigarettes which are about to be deformed during advancement past the monitoring device 51. Thus, if each of the cigarettes 54 approaching the monitoring device 51 would have an ideal circular cross-sectional outline, advance determination of the diameters A ahead of the device 51 would be unnecessary because mechanical deformation of each cigarette 54 would start at the same distance (matching the ideal diameter of a cigarette 54) from the deepmost portion of the flute 55 at the mechanical monitoring station. However, and since this is not the case because each cigarette 54 approaching the lever 53 is likely to be at least slightly out of round, optical determination of the diameters A ahead of the monitoring device 51 ensures that the signals denoting the extent of mechanical deformation of successive cigarettes by the lever 53 can be corrected by taking into consideration the actual diameters A of successive cigarettes before they reach the mechanical hardness testing station. It can be said that the measuring head 58 ascertains a variable reference point RP ahead of the lever 53 to thus enable the signal processing unit 63 to determine the exact extent of radial deformation of cigarettes 54 by the lever 53 in that the signal which are transmitted by the evaluating circuit 61 and are modified by the computer 64 denote the actual extent of radial deformation of each cigarette 54 regardless of the initial diameters A of such cigarettes. In other words, the reference points RP are the starting or zero points for determination of the extent of radial deformation of successive cigarettes 54 during travel past the lever 53. The construction of signal generating means forming part of the monitoring device 51 can be the same as that of the monitoring device which is disclosed in the aforementioned commonly owned U.S. Pat. No. 4,974,443 to Heitmann.

An advantage of the computer 64 is that, in its simplest form, this component of the signal processing unit 63 can be designed to furnish signals which denote the differences between the diameters A and B of successive optically scanned and mechanically tested cigarettes 54 whereby the difference A−B accurately denotes the extent of radial deformation of the cigarettes by the lever 53 and hence the actual hardness of tested articles. Thus, the number of steps which must be carried out to correct the signals from the signal generating means of the monitoring device 51 on the basis of optical scanning at the station 60 can be reduced to a minimum without affecting the accuracy and reliability of information which is displayed at 67 and/or of signals which are transmitted from the computer 64 to the trimming or equalizing device 12 in order to alter the hardness if the monitored and corrected hardness does not match an optimum value.

As described hereinabove, the signal processing unit 63 is or can be designed to ascertain a corrected hardness value for each of a short or long series of successively tested cigarettes 54. However, it is often preferred to avoid individual correction of mechanical testing of each and every cigarette 54 of the series by designing the evaluating circuit 61 with a view to furnish first signals each of which is indicative of the average (mechanically determined) hardness of two or more successive cigarettes 54, and by designing the signal generating means of the optical scanning device 57 with a view to furnish second signals each of which is indicative of the average diameter A of a number of successive cigarettes 54 advancing past the measuring head 58.

Referring again to FIG. 3, the optical scanning operation at the station 60 can be simplified by designing the measuring head 58 in such a way that it generates a single signal during advancement of a cigarette 54 past the fixed reference point FRP. However, the results of determination of the diameter A of a cigarette 54 at the scanning station 60 are much more accurate and reliable if the optical testing involves the generation of a set of signals (as denoted by the curve 68 in the window 69) and by selecting the weakest or the strongest signal (particularly the signal at 68a denoting the minimum distance of an article 54 from the point FRP) as that (second) signal which is transmitted to the evaluating circuit 62 and thence to the computer 64.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of our contribution to the art and, therefore, such adaptations should and are intended to be comprehended within the meaning and range of equivalence of the appended claims.

We claim:

1. A method of ascertaining the hardness of elastically deformable elongated substantially cylindrical articles of the tobacco processing industry, the articles having different thicknesses deviating to different extents from a desired thickness and each article having an external surface and a longitudinal axis, comprising the steps of advancing a series of articles in a predetermined direction along a predetermined path wherein the longitudinal axes of the articles are at least substantially normal to said direction; subjecting the articles of said series to elastic deformation in a first portion of said path, including applying to the articles a predetermined deforming force radially of the articles whereby the articles develop depressions and the extent of elastic deformation is indicative of the hardness of deformed articles; monitoring the extent of elastic deformation and generating first signals denoting the monitored deformation; determining the deviation of the thickness of the articles of said series from the desired thickness in a second portion of said path upstream of said first portion and generating second signals denoting the extent of deviation of determined thickness from the desired thickness; and modifying said first signals in dependency on the respective second signals so that the thus modified first signals are indicative of the hardness of the respective articles irrespective of the thickness thereof.

2. The method of claim 1, wherein said determining step comprises measuring the distance of external surfaces of articles from a predetermined fixed reference point, said second signals being indicative of the measured distance and of the thickness of the respective articles.

3. The method of claim 1, wherein said advancing step comprises conveying the articles along the first portion of said path on a mobile support and said determining step comprises further measuring the distance of the support from a fixed reference point.

4. The method of claim 1, wherein said monitoring step includes ascertaining the thickness of deformed articles in said first portion of said path and said determining step comprises determining the thickness of articles in said second portion of said path and the difference between the thicknesses of an article in the first and second portions of said path.

5. The method of claim 1 of ascertaining the hardness of articles containing moist tobacco, further comprising the steps of monitoring the moisture content of tobacco in the articles, generating third signals denoting the monitored moisture content, and modifying said first signals in dependency on said third signals.

6. The method of claim 1 of ascertaining the hardness of tobacco-containing articles, further comprising the steps of monitoring the temperature of tobacco in the articles, generating additional signals denoting the monitored temperature, and modifying said first signals in dependency on said additional signals.

7. Apparatus for ascertaining the hardness of elastically deformable elongated substantially cylindrical articles of the tobacco processing industry, the articles having different thicknesses deviating to different extents from a desired thickness and each article having an external surface and a longitudinal axis, comprising means for advancing a series of articles in a predetermined direction along a predetermined path wherein the longitudinal axes of the articles are at least substantially normal to said direction; a deforming device having means for subjecting the articles of said series to elastic deformation in a first portion of said path, including means for applying to the articles a predetermined deforming force radially of the articles whereby the articles develop depressions and the extent of elastic deformation is indicative of the hardness of deformed articles; means for determining the deviation of the thickness of the articles of said series from the desired thickness in a second portion of said path upstream of said first portion, including means for generating second signals denoting the extent of deviation of determined thickness from the desired thickness; and signal processing means including means for modifying said first signals in dependency on the respective second signals so that the thus modified first signals are indicative of the hardness of the respective articles irrespective of the thickness thereof.

8. The apparatus of claim 7, wherein said determining means comprises a measuring head defining a fixed reference point adjacent the second portion of said path, said means for generating second signals comprising means for generating signals denoting the distances of the surfaces of articles in said second portion of said path from said fixed reference point, said signal generating means of said determining means comprising means for converting signals denoting said distances into signals denoting the thickness of the respective articles.

9. The apparatus of claim 8, wherein said advancing means includes an article supporting conveyor disposed at a predetermined distance from said fixed reference point, said signal processing means including a memory for third signals denoting said predetermined distance and means for generating further signals denoting the differences between said third signal and the signals denoting the distances of the surfaces of articles in said second portion of said path from said reference point.

10. The apparatus of claim 9, wherein said measuring head includes means for directing at least one beam of radiation upon articles in the second portion of said path whereby the articles reflect at least a portion of said at least one beam, and means for intercepting the reflected portion of said at least one beam.

11. The apparatus of claim 8, wherein said measuring head includes means for triangulating the deviation of the thickness of articles of the series from the desired thickness in the second portion of said path.

12. The apparatus of claim 7, wherein said signal processing means further comprises means for evaluating said first signals and means for evaluating said second signals, said modifying means comprising a computer having inputs for evaluated first and second signals and being arranged to generate signals denoting the differences between the evaluated first signals and the respective evaluated second signals.

13. The apparatus of claim 7 for ascertaining the hardness of rod-shaped articles which contain moist tobacco, further comprising means for generating third signals denoting the moisture content of tobacco in the articles, said signal processing means further including means for modifying said first signals as a function of said third signals.

14. The apparatus of claim 7, further comprising means for monitoring the temperature of rod-shaped articles and for generating additional signals denoting the monitored temperature, said signal processing means further comprising means for modifying said first signals as a function of said additional signals.

15. The apparatus of claim 7, wherein said advancing means includes at least one rotary conveyor having peripheral article-receiving flutes.

16. The apparatus of claim 15, wherein said determining means includes means for measuring the thickness of articles radially of said at least one conveyor.

* * * * *

UNITED STATES PATENT AND TRADEMARK OFFICE
CERTIFICATE OF CORRECTION

PATENT NO. : 5,347,853
DATED : September 20, 1994
INVENTOR(S) : Reinhard HOPPE, Rolf LINDEMANN and Henning MÖLLER It is certified that error appears in the above-indentified patent and that said Letters Patent is hereby corrected as shown below:

Title page, item [73], change "Hörber" to --Körber--.

Signed and Sealed this

Thirteenth Day of December, 1994

Attest:

BRUCE LEHMAN

Attesting Officer     Commissioner of Patents and Trademarks